(12) United States Patent
Marino et al.

(10) Patent No.: US 6,960,220 B2
(45) Date of Patent: Nov. 1, 2005

(54) HOOP DESIGN FOR OCCLUSION DEVICE

(75) Inventors: Joseph A. Marino, Apple Valley, MN (US); Michael P. Corcoran, Oakdale, MN (US)

(73) Assignee: Cardia, Inc., Burnsville, MN (US)

( * ) Notice: Subject to any disclaimer, the term of this patent is extended or adjusted under 35 U.S.C. 154(b) by 55 days.

(21) Appl. No.: 10/349,118

(22) Filed: Jan. 22, 2003

(65) Prior Publication Data

US 2004/0143277 A1 Jul. 22, 2004

(51) Int. Cl.[7] ............................................. A61B 17/00
(52) U.S. Cl. ....................................................... 606/153
(58) Field of Search ................................. 606/153, 151, 606/152, 154, 155, 213, 215, 200, 232, 220

(56) References Cited

U.S. PATENT DOCUMENTS

| | | | |
|---|---|---|---|
| 3,874,388 A | 4/1975 | King et al. | |
| 4,007,743 A * | 2/1977 | Blake | 606/232 |
| 4,917,089 A | 4/1990 | Sideris | 606/215 |
| 5,108,420 A | 4/1992 | Marks | 606/213 |
| 5,171,259 A | 12/1992 | Inoue | 606/213 |
| 5,284,488 A | 2/1994 | Sideris | 606/213 |
| 5,334,137 A | 8/1994 | Freeman | 604/8 |
| 5,334,217 A * | 8/1994 | Das | 606/213 |
| 5,397,331 A | 3/1995 | Himpens et al. | 606/151 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,634,936 A | 6/1997 | Linden et al. | 606/213 |
| 5,702,421 A | 12/1997 | Schneidt | 606/213 |
| 5,709,707 A | 1/1998 | Lock et al. | 606/213 |
| 5,725,552 A | 3/1998 | Kotula et al. | 606/213 |
| 5,741,297 A | 4/1998 | Simon | 606/213 |
| 5,904,703 A * | 5/1999 | Gilson | 606/213 |
| 6,024,756 A | 2/2000 | Huebsch et al. | 606/213 |
| 6,174,322 B1 * | 1/2001 | Schneidt | 606/213 |
| 6,206,907 B1 | 3/2001 | Marino et al. | 606/215 |
| 6,379,368 B1 | 4/2002 | Corcoran et al. | 606/153 |

FOREIGN PATENT DOCUMENTS

GB 2 269 321 A 9/1994

* cited by examiner

Primary Examiner—Vy Bui
(74) Attorney, Agent, or Firm—Kinney & Lange, P.A.

(57) ABSTRACT

The present invention is an occlusion device having a support hoop. The support hoop increases the ability of the occlusion device to form a seal around the defect and adds additional structural strength to the device by allowing distribution of pressure along a 360° continuum.

30 Claims, 3 Drawing Sheets

HOOP DESIGN FOR OCCLUSION DEVICE

CROSS-REFERENCE TO RELATED APPLICATION(S)

This application is related to U.S. Patent application entitled Articulated Center Post, Ser. No. 10/348,856, Occlusion Device Having Five or More Arms, Ser. No. 10/349,118, Septal Stabilization Device, Ser. No. 10/349,744, and U.S. Patent Application entitled Laminated Sheets for Use in a Fully Retrievable Occlusion Device, Ser. No. 10/348,864, all filed on even date herewith.

BACKGROUND OF THE INVENTION

This invention relates to an occlusion device for the closure of physical apertures, such as vascular or septal apertures. More specifically, this invention relates to an occlusion device for the heart having a support hoop which allows the device to form a better seal around the aperture and evenly distributes pressure to the tissue surrounding the aperture.

The heart is generally comprised of four chambers, the left and right atrium and the left and right ventricle. Separating the left and right sides of the heart are two walls, or septa. The wall between the two atria is the interatrial septum, and the wall between the two ventricles is the interventricular septum. There are several defects which can affect the septa of both children and adults, including patent ductus arteriosus, patent foramen ovale, atrial septal defects (ASDs), and ventricular septal defects (VSDs).

Normally, permanently repairing certain cardiac defects in adults and children requires open heart surgery, a risky, expensive, and painful procedure. To avoid the risks and discomfort associated with open heart surgery, modern occlusion devices have been developed that are small, implantable devices capable of being delivered to the heart through a catheter. Rather than surgery, a catheter inserted into a major blood vessel allows an occlusion device to be deployed by moving the device through the catheter. This procedure is performed in a cardiac cathlab and avoids the risks and pain associated with open heart surgery. These modern occlusion devices can repair a wide range of cardiac defects, including patent foramen ovale, patent ductus arteriosus, atrial septal defects, ventricular septal defects, and may occlude other cardiac and non-cardiac apertures.

There are currently several types of occlusion devices capable of being inserted via a catheter including button devices, collapsible umbrella-like structures, and plug-like devices. Occlusion devices with umbrella-like structures use a system of small metal wires to hold the occlusion device in place. Once deployed, some of the metal wires may experience more or less stress as a result of the uneven topography surrounding the defect. In such cases, the wires which experience a high static load due to their placement experience high degrees of stress. Several problems may result from this continuous stress, including fatigue failure of the wires which causes them to fracture or break. Broken wires increase the likelihood of damage to the surrounding tissue and lead to patient anxiety.

Another issue caused by the wires is the distribution of pressure along the wires and at their tips. The wires must provide enough pressure against the adjacent tissue to ensure the occlusion device remains in place and that it properly occludes the defect. However, if the wires are not seated properly, or are experiencing high static load due to their placement over uneven topography, the increased pressure may damage the surrounding tissue. In addition, the pressure tends to be highest at the tips of the wires, which may result in the tips poking through tissue or causing damage to it.

Another potential problem with these devices is failure to provide a good seal at the defect. Lack of a good seal can be caused when the wires do not seat properly, or in cases where one or more of the wires pokes back through a defect. If an occlusion device does not provide a good seal, blood will continue to flow through the defect even after the occlusion device has been deployed. Occlusion devices that fail to provide a good seal fail to eliminate health concerns associated with the cardiac defects that they are supposed to treat.

Thus, there is a need in the art for an occlusion device that will effectively occlude cardiac defects and distribute static pressure, thereby increasing the life of the device and sealing ability while reducing the likelihood of damage to the surrounding tissue.

BRIEF SUMMARY OF THE INVENTION

The present invention allows occlusion devices to more effectively close a physical anomaly. The present invention is an occlusion device having a support hoop. The addition of a support hoop to an occlusion device addresses both pressure problems and sealing concerns. The support hoop increases the ability of the occlusion device to form a seal around the defect and adds additional structural strength to the device by allowing distribution of pressure along a 360° continuum. The distribution of pressure reduces static load on any single part of the device and also distributes pressure more evenly to the tissue surrounding the defect. As a result, the support hoop hugs the tissue surrounding the defect, leading to better sealing capabilities, minimized tissue damage, and increased life span of the device.

DETAILED DESCRIPTION

Figure 1:
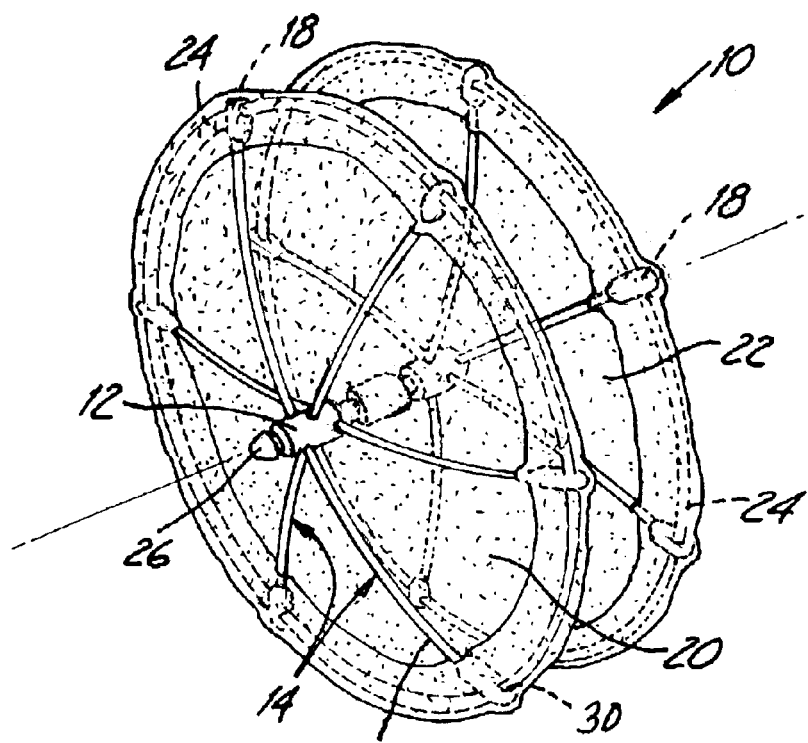
FIG. 1 is a perspective view the top of an occlusion device having a support hoop.

FIG. 1 is a top perspective view of an occlusion device 10. The occlusion device 10 comprises a center post 12, first fixation device 14, wire arms 16, and endcaps 18. The first fixation device 14 is connected to the center post 12 and comprises the six 16 wire arms which are capped with the endcaps 18. The occlusion device also comprises a first sheet 20, a second sheet 22, and wire hoops 24. The hoops 24 surround the perimeter of the first and second sheets 20, 22 and pass through holes 30 in the endcaps 18. A groove 26 is located near the tip of the center post 12.

Figure 2:
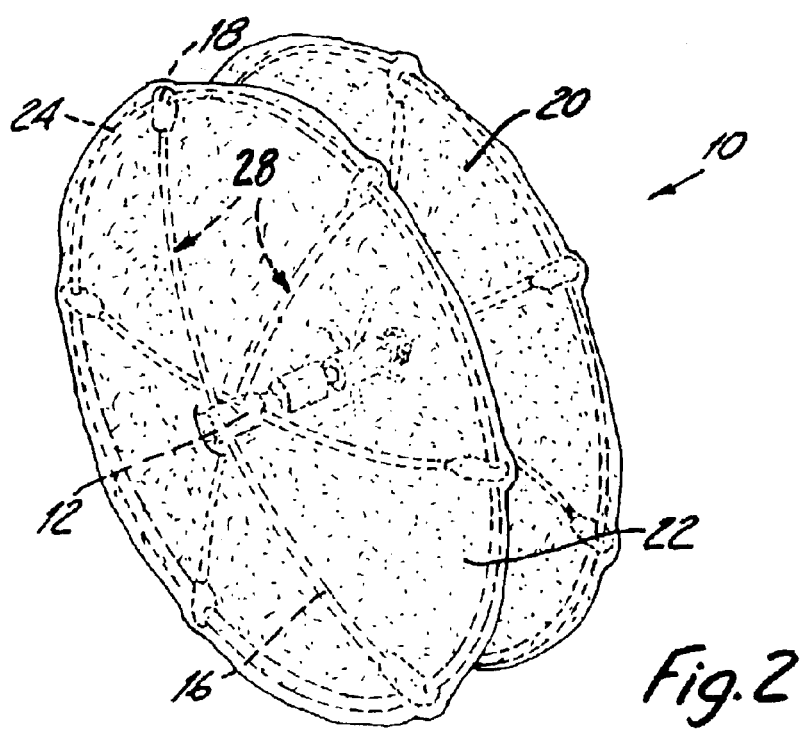
FIG. 2 is a perspective view of the bottom of an occlusion device having a support hoop.

FIG. 2 is a bottom perspective view of the occlusion device 10. Shown in FIG. 2 is the center post 12, second sheet 22, and a second fixation device 28. The second fixation device 28 is also comprised of six arms 16 which are capped by endcaps 18. Also visible in FIG. 2 is the first sheet 20.

Unlike the first fixation device 14 which is located on an outer side of the first sheet 20, the second fixation device 28 is located on an inner side of the second sheet 22. However, the device is not so limited, and the fixation devices 14, 28 may be located on the outer side of the sheets 20, 22, on the inner side of the sheets 20, 22, or any combination thereof.

The first and second fixation devices 14, 28 are connected to the center post 12. One method of connecting the first and second fixation devices 14, 28 to the post 12 is to provide the center post 12 with drill holes through which the fixation devices 14, 28 pass. When connected to the center post 12 using holes drilled through the center post 12, the fixation devices 14, 28 may be formed of three wires. The three wires create the six arms 16 because the post 12 divides each wire into two arms 16 when the wire passes through the center post 12. The endcaps 18 located at the distal ends of the arms 16 serve to minimize damage to the surrounding tissue.

The sheets 20, 22 are connected to the device 10 at the center post 12 and at the fixation devices 14, 28. The sheets 20, 22 may be connected to the fixation devices 14, 28 using any suitable method. One method of attaching the sheets 20, 22 to the fixation devices 14, 28 is to suture the sheets 20, 22 to the arms 16 of the fixation devices 14, 28. The endcaps 18 are provided with drilled holes 30 through which the hoop 24 can pass for attachment.

The device 10 is configured to be deployed through a catheter, and the knob 26 on the center post 12 is configured to allow the device 10 to be grasped by a forceps as it is guided through the catheter. Only one side of the center post 12 needs a knob 26. More specifically, the device 10 is constructed so that the fixation devices 14, 28 are easily collapsible about the center post 12. Due to this construction, the device 10 can be folded so that the first fixation device 14 is folded in the axial direction and the second fixation device is folded in an opposite axial direction. The first and second sheets 20, 22, attached to the fixation devices 14, 28, and can likewise collapse as the fixation devices 14, 28 are folded. Likewise, the hoops 24 are also flexible and configured to collapse.

Once the device 10 is deployed, the fixation devices 14, 28 serve to exert pressure on the sheets 20, 22 which form a seal around the defect. To ensure the device 10 exerts enough pressure to seal the defect, the devices 14, 28 are made of a suitable material capable of shape memory, such as nickel-titanium alloy, commonly called Nitinol. Nitinol is preferably used because it is commercially available, very elastic, non-corrosive and has a fatigue life greater than that of stainless steel. To further ensure that the fixation devices 14, 28 do not suffer from fatigue failures, one embodiment of the present invention relies on making the wire fixation devices 14, 28 of stranded wire or cables.

The wire arms 16 are preferably subjected to a precise pre-shaping to give them a "shape memory." The pre-shaping can be done either by machining, heat treating, or both. The shape memory helps to hold the strands together when the arms 16 are formed of stranded wire or cable, and can be used to add pretension to the arms 16 so that they "remember" their shape even after undergoing a strong deformation when the device 10 is passed through a catheter. The endcaps 18 may further serve to prevent potential unraveling of the arms 16 when the arms are formed of stranded wire or cable.

The support hoops 24 are also made of a suitable material capable of shape memory, such as nickel-titanium alloy, like Nitinol. The hoops 24 may be constructed of a single wire or stranded wire. Similar to the wire arms, the support hoops 24 may also be heat shaped or machine shaped so that they have shape memory. The shape memory ensures that the hoop 24 will lay flat against the tissue surrounding the defect once it is deployed and that the hoops 24 are properly sized. In addition, pre-shaping ensures that the hoops 24 will resume the proper shape once they leave the catheter.

The support hoops 24 allow the device 10 to hug the tissue surrounding the defect, creating a more uniform seal around the opening of the defect, which improves the sealing capabilities of the occlusion device 10 while reducing the potential for intense pressure in any one area. This allows for pressure to be distributed around a 360° continuum. The fixation devices 14, 28 serve to exert pressure on the sheets 20, 22 to form a seal around the defect. Without the hoops 24, the highest points of pressure are the six or eight pressure points where the tips of the arms 16 press against the tissue surrounding the defect. Instead of having six or eight pressure points, the support hoops 24 more evenly distribute pressure in a continuous circle, decreasing the possibility that pressure will be exerted primarily in any one contact point. By distributing pressure more evenly, it is unlikely that portions of the occlusion device 10 that exert the most pressure on the tissue, such as the tips of the arms 16, will poke through the tissue or poke through the defect.

The sheets 20, 22 are preferably formed of a medical grade polymer. One suitable material is DACRON®. Preferably, the sheets 20, 22 are formed of a high density polyvinyl alcohol (PVA) foam, such as that offered under the trademark IVALON®. To minimize the chance of the stabilization device 10 causing a blood clot, the sheets 20, 22 may be treated with a thrombosis-inhibiting material. One such suitable material is heparin.

The size of the sheets 20, 22 may vary to accommodate various sizes of defects. In some instances, it may be desirable to form the sheets 20, 22 so that they are not both the same size. For instance, one sheet and its associated fixation device can be made smaller than the corresponding sheet and its associated fixation device. This is particularly useful in situations where the occlusion device 10 is to be placed at a location in the heart which is close to other nearby cardiac structures. Making the sheets 20, 22 different sizes may assist in providing optimal occlusion of a defect, without affecting other structures of the heart which may be nearby.

The other parts of the stabilization device 10 are likewise formed of suitable materials. More specifically, the center post 12 may be formed of platinum-iridium and the endcaps 18 may be formed of titanium. However, the invention is not limited to these materials and any suitably biocompatible materials will suffice.

Though not immediately evident in FIGS. 1 and 2, the arms 16 vary slightly in length. This is so that when the device 10 is folded, it fits more easily into a catheter. Making the arms 16 of slightly different lengths ensures the endcaps 18 are not all located at the same place when the device 10 is folded into a catheter, which would make the device 10 too bulky to fit into a small diameter catheter. In addition, though shown with six arms 16, the device 10 is not so limited. Rather, the device 10 may be comprised of four arms, or may be comprised of anywhere from five, six, eight, ten, or even more arms.

Another feature of the occlusion device 10 is that it is fully retrievable. In situations where the occlusion device 10 is not properly deployed and must be retrieved into the catheter 50, it is possible to withdraw the occlusion device 10 back into the catheter 50 by grasping either the center section 12 or by grasping any one of the arms 16. To allow the device 10 to be retrievable, as well as ensure that the device 10 fits into as small a diameter catheter as possible, it is important to ensure that the arms 16 are not of a length that results in the tips 18 clustering at the same location. If the tips 18 all occur at the same location when the device 10 is inside the catheter, the device 10 will become too bulky to allow it to be easily moved through the catheter. To make the device 10 retrievable, it is possible to vary the length of the upper arms from the length of the lower arms 16 so that when the device 10 is retrieved, the endcaps 18 on the upper arms 16 do not cluster at the same location as the endcaps 18 on the lower arms 16.

Figure 3:
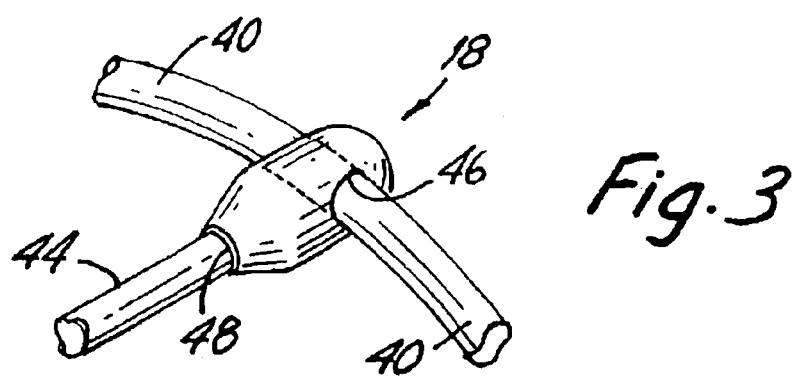
FIG. 3 is a perspective view of an endcap in place on a hoop.

FIG. 3 shows an enlarged perspective view of an endcap 18 in place on a hoop. Shown is an endcap 18, a portion of a support hoop 40, a portion of a wire support arm 44, a hole 46, and an end cavity 48. The support hoop 40 passes through holes 46 drilled crosswise through the endcap 18. The wire support arm 16 is inserted into an end cavity 48 located at the base of the endcap 18.

The endcaps 18 cap the wire support arms 16 to protect tissue and prevent unraveling of the wire support arms 16 if they are stranded. The tip of the endcap 18 is rounded to reduce the potential for trauma to the tissue surrounding a defect. The endcaps 18 also serve as a location for the support hoop 40 to attach to the occlusion device 10. By providing a link between the wire support arms 16 and the support hoop 40, the endcaps 18 allow for better distribution of pressure once the device 10 is deployed and exerting pressure on the tissue surrounding a defect.

Figure 4A:
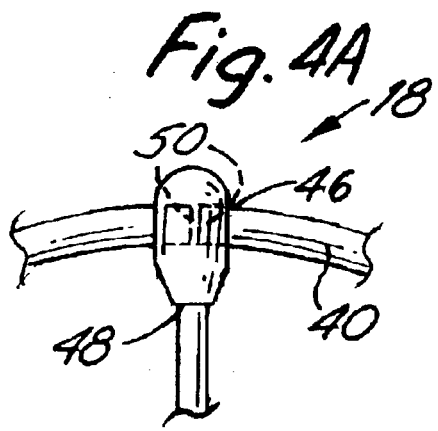
FIG. 4A is a top view of an endcap which demonstrates one method of closing a hoop.
Figure 4B:
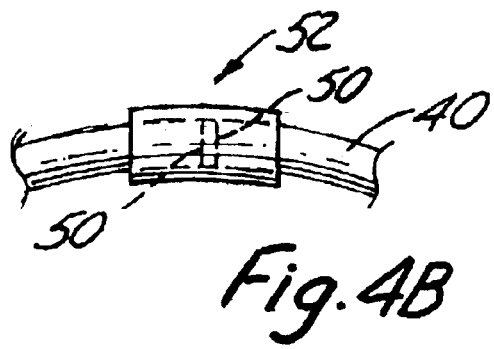
FIG. 4B is a top view of a coupler which demonstrates one method of closing a hoop.

FIGS. 4A and 4B show enlarged views of two examples of how a support hoop 24 can be closed so that it forms a circle. FIG. 4A shows a portion of a support hoop 40 which has been closed inside an endcap 18. Shown is an endcap 18, a portion of a support hoop 40, ends of the support hoop 50, and an end cavity 48.

The support hoop 24 is typically formed of a single wire. To form the hoop 24, the wire must be closed in order to provide a 360° seal around the defect and evenly distribute pressure. The support hoop 24 may be closed after it has been threaded through the endcaps 18. In FIG. 4A, the ends of the support hoop 50 meet after passing through holes 46 in the endcap 18. The ends of the support hoop 50 are secured in the endcap 18 by using any suitable method, such as crimping, welding, or adhesive. By joining the ends of the support hoop 50 inside an endcap, 18 no additional material must be added to the occlusion device 10, thereby keeping the size and weight of the device 10 to a minimum.

FIG. 4B shows a second example of how a support hoop 24 may be closed. FIG. 4B shows a portion of a support hoop 40 which has been closed inside a coupler 52. Shown is a portion of a support hoop 40, ends of the support hoop 50 and a coupler 52. In this example, the coupler 52 is a small hollow tube with a diameter slightly larger than that of the wire used to construct the support hoop 24. The ends of the support hoop 50 are inserted in the coupler 52 where they meet. The coupler 52 can then be crimped or welded so that the ends of the support hoop 50 remain inside the coupler 52.

Other possible methods of joining the ends of the support hoop 50 may include crimping the ends 50 together or welding the ends 50 together without the use of an endcap 18 or coupler 52.

Figure 5:
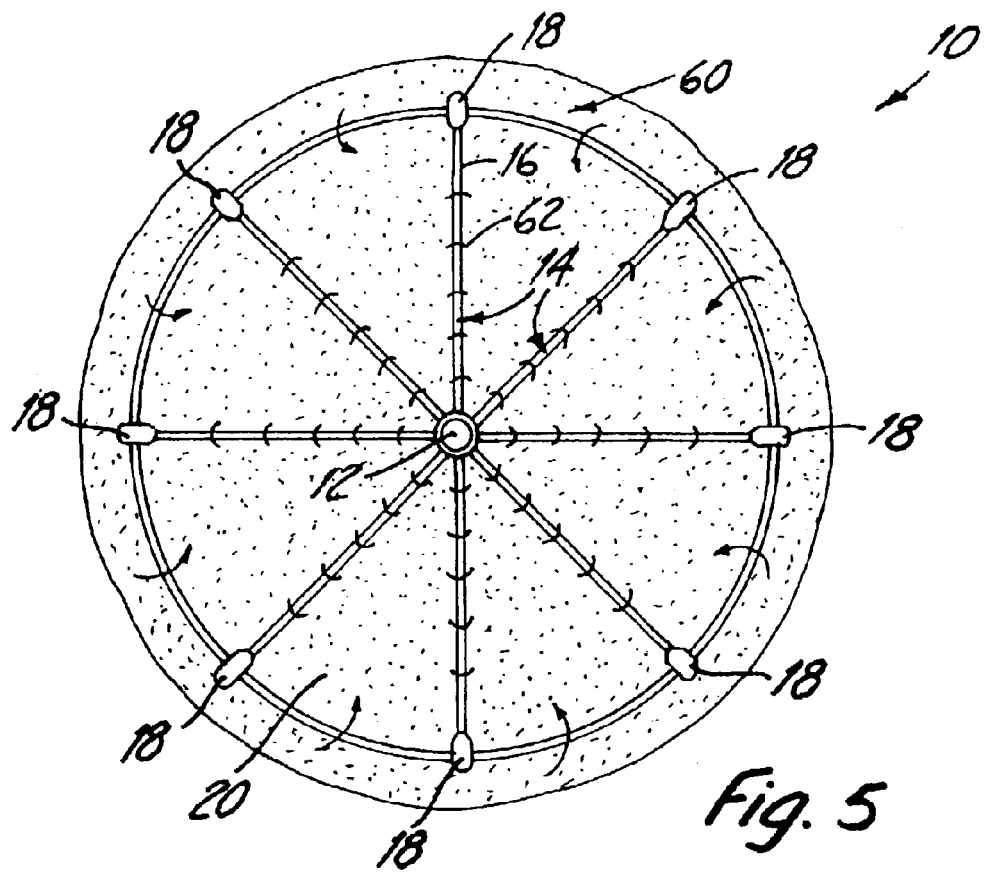
FIG. 5 is a top view of an occlusion device having a hoop which demonstrates how a sail is attached to the support frame and hoop.

FIG. 5 is a top view of an occlusion device 10. FIG. 5 demonstrates how the first and second sheets 20, 22 may be attached to the device 10. Shown is the center post 12, wire fixation devices 14, 28, wire arms 16, endcaps 18, the first sheet 20, and the support hoop 24. Also shown are a reinforcement edge 60 and sutures 62.

The sutures 62 may be used to attach the first sheet 20 to the wire arms 16. Though not shown, the second sheet 22 may be attached to the wire arms 16 in the same manner. In this example, the sutures 62 transverse the wire arms 16, attaching the sheet 20 to the arms 16. The sutures may also run lengthwise along the wire arms 16 on each side of the wire arms 16 if an additional sheet of foam is provided to cover the wire arms 16 so that they are not exposed. The pieces of foam may run lengthwise down the arms 16. The two layers of foam, once sutured, form foam pockets, with the wire arms 16 inside. In addition to suturing, the foam may be connected to the arms 16 using any suitable method, such as bonding, gluing, heat treating, or laminating.

The diameter of the first sheet 20 is slightly larger than that of the support hoop 24. The larger diameter of the first sheet 20 extends beyond the support hoop 24 after it is attached to the wire arms 16 and constitutes the reinforcement edge 60. The reinforcement edge 60 allows this portion of the sheet to be folded over the support hoop 24 to form a reinforced edge of double material around the perimeter of the device 10. Once the reinforcement edge 60 has been folded over the support hoop 24, it can be held in place either by sutures, heat treatment, or another suitable method. Alternatively, the reinforcement edge 60 is a foam ring manufactured separately from the first and second sheets 20, 22. The foam ring folds over the perimeter of the device 10 and is attached in any suitable manner such as suturing, bonding, gluing, heat treating, or laminating.

Once attached, the reinforcement edge 60 covers the exposed edges of the occlusion device 10. The reinforcement edge 60 acts as a cushion between the exposed metal edges of the occlusion device 10 and the tissue surrounding the defect, providing extra protection from pressure that the device 10 exerts on the tissue.

The reinforcement edge 60 also serves to secure the sheets 20, 22 to the device 10. Often, in order to adequately seal the defect, the wire arms 16 must bend to accommodate the contours of the heart. Because the sheets 20, 22 are sewn to wire arms, the sheets 20, 22 must accommodate the bending of the wire arms 16. In this case, the sheets 20, 22 experience constant tension and tearing may occur, especially where the sutures 62 are located. If the sheets 20, 22 tear, the sealing ability of the occlusion device may be compromised. The reinforcement edge 60 helps to prevent the first and second sheets 20, 22 from tearing at the areas where they are attached to the device 10. Because the reinforcement edge 60 overlaps the hoop 24 and is then affixed to the rest of the sheet 20, 22, it adds an additional 360° of continuous attachment of the sheets 20, 22 to the frame of the device 10 reducing the likelihood of tearing or detachment. The additional 360° of attachment helps to distribute the tension along a continuum instead of focusing tension at discrete attachment sites like the suture points.

Figure 6:
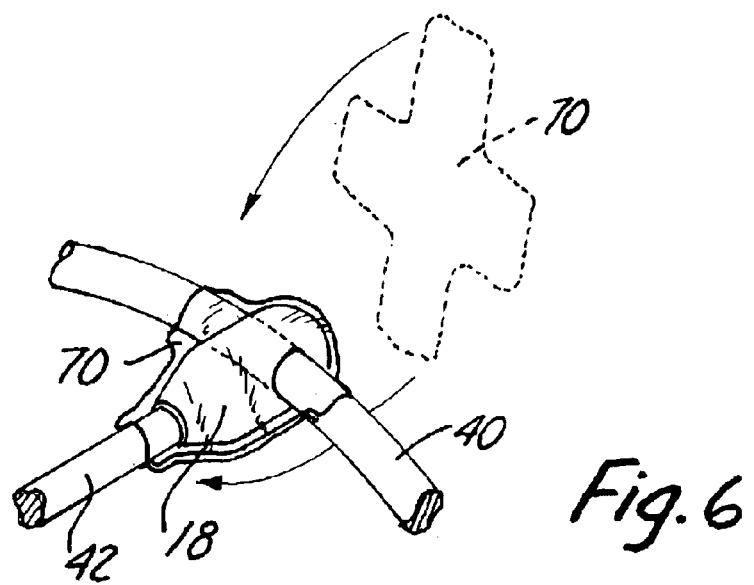
FIG. 6 is a perspective view of a foam patch in place on an occlusion device.

FIG. 6 demonstrates an alternative method of reinforcing the occlusion device 10. FIG. 6 shows reinforcement using a patch 70. Shown is a patch 70, a portion of a support hoop 40, a portion of a wire arm 42, and an endcap 18.

The patch 70 is constructed of foam and is configured to fit over the endcap 18. In this example, the patch 70 is shaped like a cross which enables it to cover both sides of the endcap 18 and a small portion of the support hoop 40 where the hoop 40 extends out of the endcap 18. The coverage extends to a small portion of the support hoop 40 where it extends out of the endcap 18. The patch 70 is then secured by sutures, heat treatment, laminating, or another suitable method.

The patch 70 acts as a cushion between the metal endcaps 18 of the occlusion device 10 and the tissue surrounding the defect, providing extra protection from pressure that the device 10 exerts on the tissue.

Although the present invention has been described with reference to preferred embodiments, workers skilled in the art will recognize that changes may be made in form and detail without departing from the spirit and scope of the invention. In particular, any of the applicable features disclosed in related applications U.S. Patent application entitled Septal Stabilization Device, Ser. No. 10/349,744, U.S. Patent application entitled Articulated Center Post, Ser. No. 10/348,856, Occlusion Device Having Five or More Arms, Ser. No. 10/349,118, U.S. Patent application entitled Septal Stabilization Device, Ser. No. 10/349,744, and U.S. patent application entitled Laminated Sheets for Use in a Fully Retrievable Occlusion Device, Ser. No. 10/348,864, filed on even date herewith, may be of use in the present invention. Each of these applications is hereby incorporated by reference.

What is claimed is:

1. An occlusion device for occluding a septal defect, the occlusion device comprising:
    a center post;
    a first occluding body connected to an end of the center post, wherein the first occluding body comprises:
        a continuous wire hoop at its outer edge;
        a set of arms connected between the center post and the hoop; and
        a first sheet attached to the continuous wire hoop and the set of arms, wherein the sheet comprises a reinforced edge forming a double layer of material which covers the hoop;
    a second occluding body connected to an opposite end of the center post, wherein the second occluding body comprises;
        a continuous wire hoop at its outer edge;
        a set of arms connected between the center post and the hoop; and
        a second sheet attached to the continuous wire hoop and the set of arms, wherein the sheet comprises a reinforced edge forming a double layer of material which covers the hoop.

2. The occlusion device of claim 1 wherein the hoop is made of nickel titanium.

3. The occlusion device of claim 2 wherein the hoop is formed from a single wire.

4. The occlusion device of claim 3 wherein the hoop is formed of stranded wire.

5. The occlusion device of claim 1 and further comprising a coupler for joining both ends of the hoop.

6. The occlusion device of claim 2 wherein the hoop is formed by welding together two ends of the hoop.

7. The occlusion device of claim 2 wherein the hoop is formed by crimping together two ends of the hoop.

8. An occlusion device, the device comprising:
    a center post;
    first and second fixation devices emanating radially from the center post;
    first and second continuous wire support hoops located at outer ends of the first and second fixation devices, respectively; and
    first and second sheets attached to the first and second fixation devices and the first and second continuous wire support hoops, wherein each sheet comprises a reinforced edge forming a double layer of material which covers the support hoops.

9. The occlusion device of claim 8 wherein the hoops are formed from a wire.

10. The occlusion device of claim 9, wherein the wire is made of nickel titanium.

11. The occlusion device of claim 10 wherein the wire is formed of stranded wire.

12. The occlusion device of claim 9 and further comprising a coupler for joining both ends of the wire.

13. The occlusion device of claim 9 wherein the hoops are formed by welding together two ends of the wire.

14. The occlusion device of claim 9 wherein the hoops are formed by crimping together two ends of the wire.

15. The occlusion device of claim 8 wherein the outer ends of the first and second fixation devices comprise end caps and the hoops connect to the first and second fixation devices at the end caps.

16. An occlusion device for the closure of a physical anomaly, the device comprising:
    an articulated center post having distal and proximal ends;
    a first set of support arms extending from the distal end of the center post;
    a first sheet attached to the first set of arms;
    a first continuous wire hoop attached to outer ends of the first set of arms and the first sheet, wherein the first sheet comprises a reinforced edge forming a double layer of material which covers the hoop;
    a second set of support arms extending from the proximal end of the center post;
    a second sheet attached to the second set of support arms; and
    a second continuous wire hoop attached to outer ends of the second set of arms and the second sheet, wherein the second sheet comprises a reinforced edge forming a double layer of material which covers the hoop.

17. The occlusion device of claim 16 wherein the first and second hoops are formed from nickel titanium.

18. The occlusion device of claim 17 wherein the first and second hoops are formed from a single wire.

19. The occlusion device of claim 16 wherein the first and second hoops are formed from stranded wire.

20. The occlusion device of claim 16 wherein the first and second arms comprise end caps and first and second hoops are attached to the first and second arms at the end caps.

21. An occlusion device, the device comprising:
    a center connection;
    a first collapsible support frame which comprises a first set of arms extending outward from the center connection and a continuous wire support hoop connected to outer ends of the first set of arms;
    a second collapsible support frame which comprises a second set of arms extending outward from the center connection and a continuous wire support hoop connected to outer ends of the second set of arms;
    a first sheet attached to the first collapsible support frame, wherein the first sheet comprises a reinforced edge forming a double layer of material which covers the continuous wire support hoop connected to the outer ends of the first set of arms; and
    a second sheet attached to the second collapsible support frame, wherein the second sheet comprises a reinforced edge forming a double layer of material which covers the continuous wire support hoop connected to the outer ends of the first set of arms.

22. The occlusion device of claim 21 wherein the first and second collapsible support frames comprise end caps on the outer ends of the arms through which the support hoops attach to the support frames.

23. The occlusion device of claim 21 wherein the hoops are formed from nickel titanium.

24. The occlusion device of claim 23 wherein the hoops are formed from stranded wire.

25. The occlusion device of claim 21 wherein the hoops are formed from a single wire.

26. An occlusion device for the closure of a physical anomaly, the device comprising:

a center connection having distal and proximal ends;

a first set of support arms extending from the distal end of the center connection;

a first sheet attached to the first set of arms;

a first continuous wire hoop attached to outer ends of the first set of arms and the first sheet, wherein in first sheet comprises a reinforced edge forming a double layer of material which covers the hoop;

a second set of support arms extending from the proximal end of the center connection;

a second sheet attached to the second set of support arms; and a second continuous wire hoop attached to outer ends of the second set of arms and the second sheet, wherein in second sheet comprises a reinforced edge forming a double layer of material which covers the hoop.

27. The occlusion device of claim 26 wherein the first and second hoops are formed from nickel titanium.

28. The occlusion device of claim 27 wherein the first and second hoops are formed from a single wire.

29. The occlusion device of claim 26 wherein the first and second hoops are formed from stranded wire.

30. The occlusion device of claim 26 wherein the first and second arms comprise end caps and first and second hoops are attached to the first and second arms at the end caps.

* * * * *